United States Patent [19]

Pauly

[11] 4,263,223
[45] Apr. 21, 1981

[54] SYNTHESIS OF 4,4'-DICYANO-POLYHALO-DIPHENOXY-ALKANES

[75] Inventor: Marc Pauly, Chateau Salins, France

[73] Assignee: Laboratoires Serobiologiques S.A., Pulnoy, France

[21] Appl. No.: 789,200

[22] Filed: Apr. 20, 1977

[30] Foreign Application Priority Data

Apr. 27, 1976 [FR] France .................. 76 12454

[51] Int. Cl.³ .......................... C07C 121/75
[52] U.S. Cl. .................. 260/465 F; 568/442; 564/259
[58] Field of Search ........... 260/465 F, 566 A, 600 R, 260/564 R

[56] References Cited

U.S. PATENT DOCUMENTS 3,444,236   5/1969   Nishizawa et al. .............. 260/465 F
4,064,169  12/1977   Hamano et al. .................. 260/564 R

FOREIGN PATENT DOCUMENTS 598911  3/1948  United Kingdom .

*Primary Examiner*—Dolph H. Torrence
*Attorney, Agent, or Firm*—Silverman, Cass & Singer, Ltd.

[57] ABSTRACT

A chemical compound of the formula:

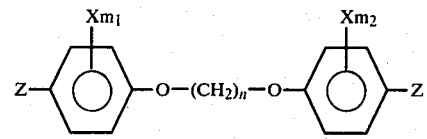

wherein X is a halogen selected from bromine, chlorine, iodine and fluorine, and preferably bromine; Z is selected from the group constituted by —CHO, —CH=NOH, —C≡N; n is an integer from 1 to 11; $m_1$ and $m_2$, identical or different, are integers from 1 to 4.

19 Claims, No Drawings

SYNTHESIS OF 4,4'-DICYANO-POLYHALO-DIPHENOXYAL-KANES

The present invention relates to new chemical compounds as well as a method of obtaining the same. It is also directed at an application of the said new compounds allowing other compounds to be obtained, some of which are themselves known and which are important intermediates in the manufacture of 4,4'-diamidino-polyhalo-diphenoxyalkanes usable as antiseptics and preserving and conserving agents.

The new compounds of the present invention are constituted by 4,4'-bis-formyl-polyhalo-diphenoxyalkanes of the formula:

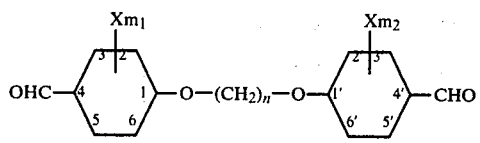

wherin X is a halogen such as bromine, chlorine, iodine or fluroine, preferably bromine, n is a whole number from 1 to 11, and $m_1$ and $m_2$ are identical or different whole numbers from 1 to 4.

According to a preferred characteristic feature of the invention, the substituted diphenoxyalkanes are symmetrical, i.e. $m_1$ and $m_2$ are equal.

Such compounds, more specifically the symmetrical compounds mentioned above, may be obtained in particular by a reaction between a 4-hydroxy-halo-benzaldehyde of the formula:

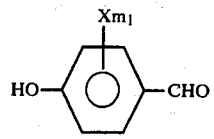

wherein X and $m_1$ have the above meanings, and an alkali metal hydroxide such as sodium hydroxide, so as to obtain an alcoholate of said alkali metal, and then by a reaction of the said alcoholate with a dihaloalkane of the formula:

wherein X is a halogen.

In a particular form of embodiment of the invention, the said compounds is constituted by 4,4'-bis-formyl-2,2'-dihalodiphenoxyalkane of the formula:

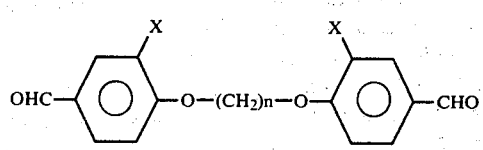

In this case, the compound is obtained from 4-hydroxy-3-halo-benzaldehyde of the formula:

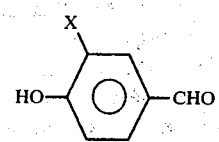

According to a preferred form of embodiment of the method of the invention, the halogen X' of the dihaloalkane used as a reactant with the alcoholate is identical with the halogen appearing as a substituent of the benzene rings.

The initial 4-hydroxy-halo-benzaldehyde of the formula:

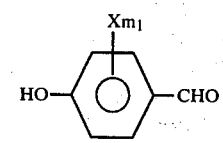

can be obtained by a reaction of 4-hydroxy-benzaldehyde with the halogen of the formula $X_2$ in an appropriate solvent, in particular chloroform.

An application of the compound of the present invention consists in obtaining 4,4'-dicyano-polyhalo-diphenoxyalkanes of the formula:

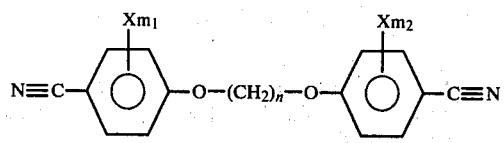

wherein X, $m_1$, $m_2$, n have the above-mentioned meanings, by a condensation of the compound of the invention with the hydroxylamine by heating in the presence of acid condensation-catalysts such as for example sodium acetate and acetic acid, so as to obtain an oxime of the formula:

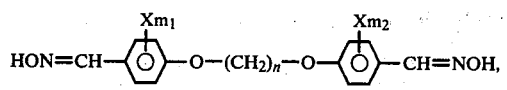

and then by a reaction of the said oxime with a dehydrating agent such as for example acetic anhydride.

The present invention also has for its object the above-mentioned oxime, of the formula:

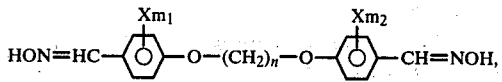

wherein X, $m_1$, $m_2$ and n have the afore-mentioned meanings, as well as a method of obtaining the said oxime from the bis-formyl compound.

According to a specific form of embodiment of the present invention, the 4,4'-dicyano-polyhaloalkanes obtained are symmetrical substituted diphenoxyhexanes, with the halogen in 2 and 2' position.

Some of the products thus obtained are already known, e.g. symmetrical compounds such as 4,4'-dicyano-2,2'-dibromo-α,γ-diphenoxypropane or 4,4'-dicyano-2,2'-dichloro-α, -diphenoxyhexanes which allow the corresponding diamidines, having important bactericidal properties, to be obtained. On the other hand, other dicyano compounds are altogether new.

As a matter of fact, the dicyano compounds—even the known ones—have always been hitherto obtained by linking together two units such as for example 4-hydroxybenzonitrile, i.e. by linking together two units including initially a cyano substituent, e.g. by the action on the said units, in the first place, of sodium ethoxide or sodium hydroxide in the presence of ethyl alcohol, and then of polymethylene bromide. None of the known earlier methods for obtaining the dicyano compound uses as initial reactant a polyhalo-diphenoxyalkane compound substituted in positions 4 and 4' of the benzene rings for a formyl group in order to substitute in the same positions 4 and 4' two nitrile groups.

Thus, the present invention also has for its object all the dicyano compounds obtained by the specific method described above.

Lastly, another object of the present invention is constituted by the new chemical compounds consisting of the dicyano compounds of the formula:

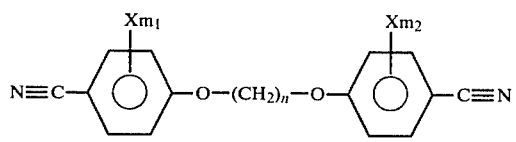

wherein X is a halogen such as chlorine, bromine, iodine or fluorine, preferably bromine, n is a whole number from 9 to 11, and $m_1$ and $m_2$ are identical or different whole numbers from 1 to 4.

Other purposes, characteristic features and advantages of the present invention will appear in the following description of several non-limitative examples of embodiment of the invention.

EXAMPLE I

Synthesis of 4-hydroxy-3-bromo-benzaldehyde

In a suspension of 61.1 g (½ mole) of 4-hydroxy-benzaldehyde in 600 ml of chloroform cooled to 0° C., there is added drop by drop 27 ml of bromine dissolved in chloroform.

The mixture is agitated for one day. It is then allowed to rest and the product precipitates.

Petroleum ether is added and a filtration is carried out.

The product is washed with water and purified by crystallization in water.

Reaction process:

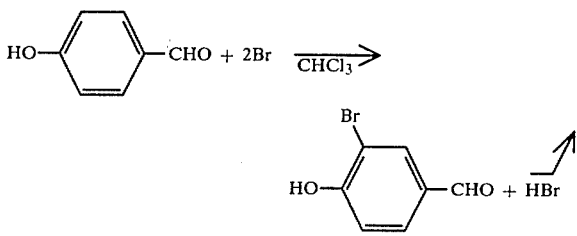

After drying there is obtained 4-hydroxy-3-bromo-benzaldehyde (yield—from 65 to 75 per cent) melting at 124° C.

EXAMPLE II

Synthesis of 4,4'-bis-formyl-2,2'-dibromo-α,ω-diphenoxyhexane

In 100.5 g (½ mole) of 4-hydroxy-3-bromo-benzaldehyde dissolved in one liter of dimethylsulphoxide, there is added 20 g of sodium hydroxide and a heating is performed at 80° C. in a current of nitrogen.

After dissolution, 38 ml of 1,6-dibromohexane are introduced. The mixture is heated for 8 hours.

After cooling, water is added and a filtration is carried out.

The product collected is washed with hot water and then crystallized in ethyl acetate.

Reaction process

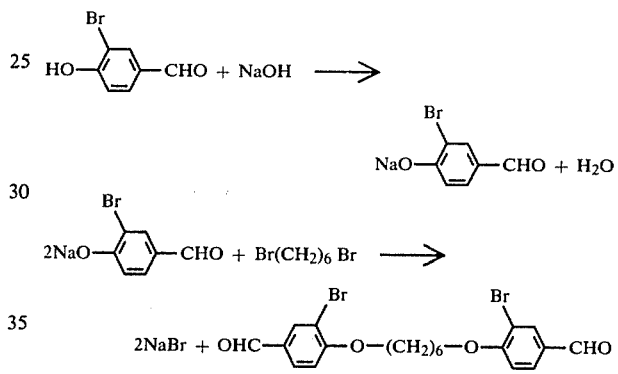

There is thus obtained 4,4'-bis-formyl-2,2'-dibromo-α,ω-diphenoxyhexane (yield—75 percent) melting at 120° C.

An alternative method consists in adding 20 g of sodium hydroxide to 100.5 g (½ mole) of 4-hydroxy-3-bromo-benzaldehyde dissolved in 300 ml of dimethylsulphoxide and in heating at 80° C. in a current of nitrogen.

In this case, the subsequent steps are identical with those just described, but the crystallization of the 4,4'-bis-formyl-2,2'-dibromo-α,ω-diphenoxyhexane is performed in acetone (2×100 ml).

EXAMPLE III

Synthesis of 4,4'-dicyano-2,2'-dibromo-α,ω-diphenoxyhexane

To 121 g (¼ mole) of 4,4'-bis-formyl-2,2'-dibromo-α,ω-diphenoxyhexane, there is added 35 g of hydroxylamine and 70 g of sodium acetate, 200 ml of acetic acid.

The mixture is heated for 3 to 4 hours.

After cooling, there is added 200 ml of acetic anhydride and a reflux heating is performed for ½ hour.

During the cooling the nitrile precipitates; it is separated by filtration and then purified by hot-water washing with sodium hydrogen carbonate.

Finally it is purified by crystallization in acetic acid.

Reaction Process

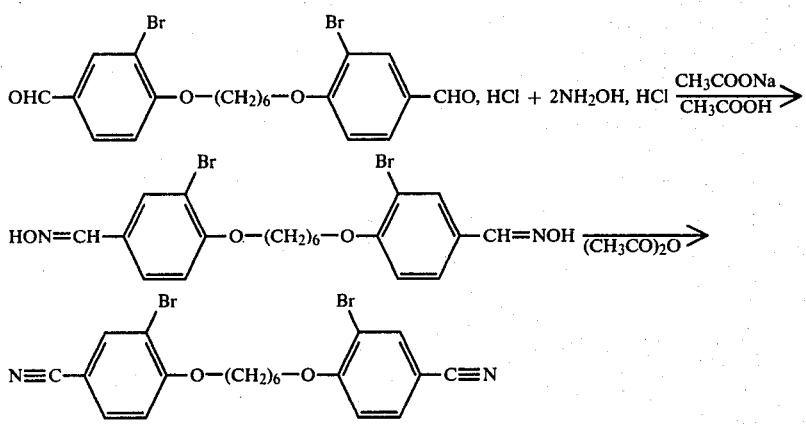

There is obtained 4,4′-dicyano-2,2′-dibromo-α, ω-diphenoxy hexane (yield—70 percent) melting at 144° C.

Of course, the invention is by no means limited to the forms of embodiment described which have been given by way of example only. In particular it comprises all the means constituting technical equivalents to the means described as well as their combinations should the latter be carried out according to its gist and used within the scope of the following claims.

What is claimed is:

1. A method of obtaining a bis-nitrile-halo-diphenoxy alkanes compound of the formula:

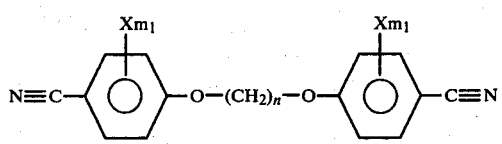

wherein X is a halogen selected from bromine, chlorine, iodine and fluorine; n is an integer from 1 to 11; and $m_1$ is an integer from 1 to 4; said method comprising the steps of:

reacting 4-hydroxy-halo-benzaldehyde of the formula:

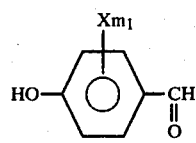

wherein X and $m_1$ are as herein above defined, with an alkali metal hydroxide, and then, reacting the resulting alcoholate with a dihalo alkane of the formula:

X′—(CH$_2$)$_n$—X′ wherein X′ is a halogen selected from bromine, chlorine, iodine and fluorine and n is an integer from 1 to 11 so as to obtain the symmetrical 4,4′bis-formyl-diphenoxy-alkane.

condensing said last mentioned compound with hydroxylamine by heating in the presence of an acid condensation catalyst to form a bis-oxime of the formula:

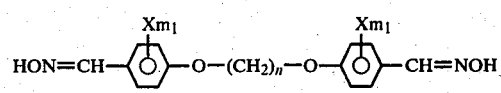

then dehydrating the bis-oxime.

2. A method according to claim 1 wherein the 4-hydroxy-halo benzaldehyde is 4-hydroxy-3-halogen-benzaldehyde of the formula:

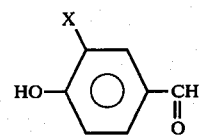

and the bis-oxime obtained being of the formula:

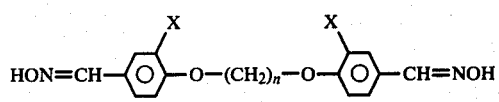

3. A method according to claim 2, wherein the said alkali metal hydroxide is sodium hydroxide.

4. A method according to claim 2, wherein X′ is equal to X.

5. A method according to claim 1 wherein the said alkali metal hydroxide is sodium hydroxide.

6. A method according to claim 1 wherein X′ is equal to X.

7. A method according to claim 1 wherein the 4-hydroxy-halo-benzaldehyde is obtained by the reaction of 4-hydroxy-benzaldehyde with the halogen of the formula X$_2$ wherein X is a halogen selected from bromine, chloride, iodine and fluorine, in an appropriate solvent, in particular chloroform.

8. The method as claimed in claim 1 in which said acid condensation catalyst is selected from the group consisting of acetic acid and sodium acetate.

9. The method as claimed in claim 1 in which the dehydration is effected by employing a dehydrating agent comprising acetic anhydride.

10. A method of obtaining a compound of the formula:

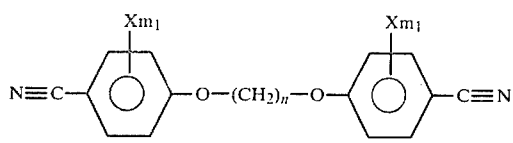

wherein X is a halogen selected from bromine, chlorine, iodine and fluorine; n is an integer from 1 to 11; and $m_1$ is an integer from 1 to 4, consisting in condensing with a dehydrating agent a compound of the formula:

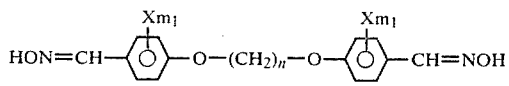

wherein n, X, $m_1$ are as herein above defined, in order to obtain 4,4'-dicyano-polyhalo-diphenoxy alkanes.

11. A method according to claim 10 wherein said dehydrating agent is acetic anhydride.

12. A method according to claim 10, wherein X is bromine.

13. A method according to claim 10, wherein $m_1$ is equal to one, and X is in the 2-and 2' positions, in order to obtain 4,4'-dicyano-2,2'-dihalo-diphenoxy alkanes.

14. A method according to claim 10 wherein $m_1$ is equal to 1, X is in the 2- and 2'-positions and n is 6, in order to obtain the 4,4'-dicyano-2,2'-dihalo-diphenoxyhexane.

15. A method of obtaining a compound of the formula:

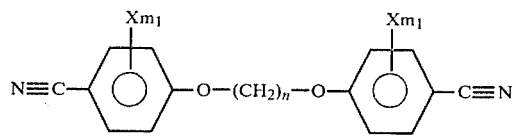

wherein X is a halogen selected from bromine, chlorine, iodine and fluorine;
n is an integer from 1 to 11; and
$m_1$ is an integer from 1 to 4,
consisting in reacting 4-hydroxy-halo-benzaldehyde of the formula:

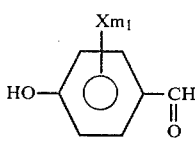

wherein X and $m_1$ are as herein above defined, with an alkali metal hydroxide so as to obtain a corresponding alcoholate of the said alkali metal, in reacting the same alcoholate with the dihalo alkane of the formula:

$$X'-(CH_2)_n-X'$$

wherein X' is a halogen and n is as herein above defined, in separating the thus obtained symmetrical 4,4'-bis-formyl-polyhalodiphenoxy alkanes of the formula:

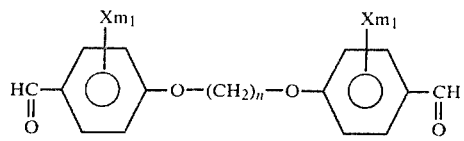

wherein X, $m_1$ and n are as herein above defined, then in condensing said symmetrical 4,4'-bis-formyl-polyhalodiphenoxy alkanes with hydroxylamine by heating in the presence of an acid-condensation catalyst, so as to form in situ in the reaction mixture the corresponding symmetrical oxime of the formula:

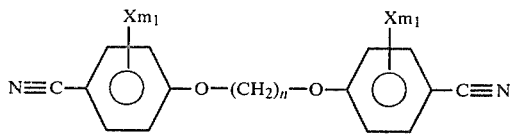

wherein X, $m_1$, n are as herein above defined, and thereafter in condensing in said reaction mixture the said oxime, without isolating same, with a dehydrating agent so as to obtain the corresponding symmetrical 4,4'-dicyano-polyhalo-diphenoxy alkanes.

16. A method according to claim 15, wherein
    acetic acid is used as said acid-condensation catalyst while acetic anhydride is used as said dehydrating agent.

17. A method according to claim 15, wherein the aforesaid reaction of 4-hydroxy-halo-benzaldehyde with an alkali metal hydroxide and the subsequent reaction of the thus produced alcoholate are both carried out in dimethylsulfoxide.

18. A method of obtaining a compound of the formula:

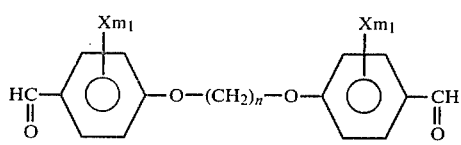

wherein X is a halogen selected from bromine, chlorine, iodine and fluorine,
n is an integer from 1 to 11; and
$m_1$ is an integer from 1 to 4 consisting in condensing a symmetrical 4,4'-bis-formyl-polyhalo-diphenoxy alkane of formula:

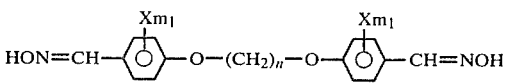

wherein X, $m_1$ and n are as herein above defined, with hydroxylamine by heating in the presence of an acid-condensation catalyst so as to form in situ in the reaction mixture the corresponding symmetrical oxime of the formula:

HON=CH—⟨ring Xm₁⟩—O—(CH₂)ₙ—O—⟨ring Xm₁⟩—CH=NOH wherein X, $m_1$, n are as herein above defined, and thereafter in condensing in said reaction mixture the said oxime, without isolating same, with a dehydrating agent so as to obtain the symmetrical 4,4'-dicyano-polyhalo-diphenoxyalkanes.

19. A method according to claim 18, wherein acetic acid is used as said acid condensation catalyst while acetic anhydride is used as said dehydrating agent.

* * * * *